US00PP20349P2

(12) United States Plant Patent
Westhoff

(10) Patent No.: US PP20,349 P2
(45) Date of Patent: Sep. 22, 2009

(54) ***LOBELIA* PLANT NAMED 'WESPURSTAR'**

(50) Latin Name: *Lobelia erinus*
Varietal Denomination: Wespurstar

(75) Inventor: Heinrich Westhoff, Südlohn (DE)

(73) Assignee: Gartenbau und Spezialkulturen Westhoff GbR, Südlohn (DE)

( * ) Notice: Subject to any disclaimer, the term of this patent is extended or adjusted under 35 U.S.C. 154(b) by 0 days.

(21) Appl. No.: 12/214,593

(22) Filed: Jun. 20, 2008

(51) Int. Cl.
*A01H 5/00* (2006.01)

(52) U.S. Cl. ..... Plt./451
(58) Field of Classification Search ..... Plt./451
See application file for complete search history.

*Primary Examiner*—Kent L Bell
(74) *Attorney, Agent, or Firm*—C. A. Whealy

(57) ABSTRACT

A new and distinct cultivar of *Lobelia* plant named 'Wespurstar', characterized by its compact, spherical and trailing plant habit; vigorous growth habit; freely branching habit and short internodes; dense and bushy plant form; continuously and freely flowering habit; and intense purple-colored flowers.

1 Drawing Sheet

Botanical designation: *Lobelia erinus.*
Cultivar denomination: 'Wespurstar'.

BACKGROUND OF THE INVENTION

The present invention relates to a new and distinct cultivar of *Lobelia,* botanically known as *Lobelia erinus* and hereinafter referred to by the name 'Wespurstar'.

The new *Lobelia* is a product of a planned breeding program conducted by the Inventor in Südlohn, Germany. The objective of the breeding program is to create new *Lobelia* cultivars with good vigor and attractive flower coloration.

The new *Lobelia* originated from a cross-pollination made by the Inventor in July, 2004 of *Lobelia erinus* 'Wespinstar', disclosed in U.S. Plant Pat. No. 17,963, as the female, or seed, parent with a proprietary seedling selection of *Lobelia erinus* identified as code number 04P721, not patented, as the male, or pollen, parent. The new *Lobelia* was discovered and selected by the Inventor as a single flowering plant with the progeny of the stated cross-pollination grown in a controlled greenhouse environment in Südlohn, Germany in June, 2005.

Asexual reproduction of the new cultivar by terminal cuttings in Südlohn, Germany since 2005, has shown that the unique features of this new *Lobelia* are stable and reproduced true to type in successive generations.

SUMMARY OF THE INVENTION

Plants of the cultivar Wespurstar have not been observed under all possible environmental conditions. The phenotype may vary somewhat with variations in environment such as temperature and light intensity without, however, any variance in genotype.

The following traits have been repeatedly observed and are determined to be the unique characteristics of 'Wespurstar'. These characteristics in combination distinguish 'Wespurstar' as a new and distinct cultivar of *Lobelia:*

1. Compact, spherical and trailing plant habit.
2. Vigorous growth habit.

3. Freely branching habit and short internodes; dense and bushy plant form.
4. Continuously and freely flowering habit.
5. Intense purple-colored flowers.

Plants of the new *Lobelia* differ from plants of the female parent, 'Wespinstar', in the following characteristics:

1. Plants of the new *Lobelia* were shorter than plants of 'Wespinstar'.
2. Plants of the new *Lobelia* have larger leaves than plants of 'Wespinstar'.
3. Flowers of plants of the new *Lobelia* are darker in color than flowers of plants of 'Wespinstar'.
4. Flowers of plants of the new *Lobelia* have larger upper petals and sepals than flowers of plants of 'Wespinstar'.

Plants of the new *Lobelia* differ from plants of the male parent selection in the following characteristics:

1. Plants of the new *Lobelia* are more freely branching than plants of the male parent selection.
2. Flowers of plants of the new *Lobelia* have larger upper petals than flowers of plants of the male parent selection.

Plants of the new *Lobelia* can be compared to plants of *Lobelia erinus* 'Hot Lilac', not patented. In side-by-side comparisons conducted in Südlohn, Germany, plants of the new *Lobelia* differed from plants of 'Hot Lilac' in the following characteristics:

1. Plants of the new *Lobelia* were smaller than plants of 'Hot Lilac'.
2. Plants of the new *Lobelia* had larger and darker green-colored leaves than plants of 'Hot Lilac'.
3. Plants of the new *Lobelia* had smaller flowers than plants of 'Hot Lilac'.
4. Flowers of plants of the new *Lobelia* had larger upper petals than flowers of plants of the 'Hot Lilac'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Lobelia*.

The photograph at the top of the sheet comprises a side perspective view of a typical flowering plant of 'Wespurstar' grown in a container.

The photograph at the bottom of the sheet is a close-up view of typical flowers of 'Wespurstar'.

DETAILED BOTANICAL DESCRIPTION

Plants used for the aforementioned photographs and following description were grown under conditions which closely approximate commercial production conditions during the spring and summer in a glass-covered greenhouse in Südlohn, Germany for 27 weeks in containers. During the production of the plants, day temperatures ranged from 20° C. to 25° C., night temperatures ranged from 16° C. to 18° C. and light levels ranged from 3,000 lux to 50,000 lux. Plants were pinched one time two weeks after planting. In the following description, color references are made to The Royal Horticultural Society Colour Chart, 2001 Edition, except where general terms of ordinary dictionary significance are used.

Botanical classification: *Lobelia erinus* 'Wespurstar'.

Parentage:

*Female parent.*—*Lobelia erinus* 'Wespinstar' disclosed in U.S. Plant Pat. No. 17,963.

*Male parent.*—Proprietary seedling selection of *Lobelia erinus* identified as code number 04P721, not patented.

Propagation:

*Type cutting.*—Terminal vegetative cuttings.

*Time to initiate roots, summer.*—About 10 to 14 days at 20° C.

*Time to initiate roots, winter.*—About 16 to 18 days at 20° C.

*Time to produce a rooted young plant, summer.*—About 21 to 24 days at 20° C.

*Time to produce a rooted young plant, winter.*—About 24 to 26 days at 20° C.

*Root description.*—Fine, fibrous.

*Rooting habit.*—Freely branching; moderately dense.

Plant description:

*Form.*—Compact, spherical and trailing plant habit. Freely branching habit with lateral branches developing at potentially every node; short internodes; dense and bushy plant habit. Vigorous growth habit.

*Plant height.*—About 20 cm.

*Plant width.*—About 51 cm.

*Lateral branch description.*—Length: About 18 cm. Diameter: About 1 mm. Internode length: About 1.3 cm. Strength: Strong. Texture: Smooth, glabrous. Color: Close to 137A.

Foliage description:

*Arrangement.*—Alternate, simple; sessile.

*Length, basal leaves.*—About 3.8 cm.

*Width, basal leaves.*—About 1.7 cm.

*Shape.*—Ovate to lanceolate.

*Apex.*—Obtuse to acute.

*Base.*—Attenuate.

*Margin.*—Crenate to entire.

*Texture, upper and lower surfaces.*—Smooth, glabrous; satiny.

*Venation pattern.*—Pinnate; arcuate.

*Color.*—Developing foliage, upper surface: Close to 147A. Developing foliage, lower surface: Close to 147B. Fully expanded foliage, upper surface: Close to 147A; venation, slightly lighter than 147A. Fully expanded foliage, lower surface: Close to 147C; venation, slightly darker than 147C.

Flower description:

*Flower arrangement/shape.*—Flowers arranged in racemes or singly at lateral apices. Flowers held mostly outwardly. Flowers persistent. Flowering freely and continuously; older flowers are overgrown by new flowers and foliage; typically 12 to 14 flowers per inflorescence. Flowers not fragrant. Flowers tubular with three lower petals and two upper petals.

*Natural flowering season.*—Spring until frost in the Germany.

*Flower longevity on the plant.*—Longevity of individual flowers is highly dependent on weather conditions; typically about one week.

*Inflorescence height.*—About 20 cm.

*Inflorescence diameter.*—About 7 cm.

*Flower diameter.*—About 1.9 cm.

*Flower depth (height).*—About 1.9 cm.

*Flower throat diameter.*—About 3.6 mm.

*Flower tube length.*—About 7.8 mm.

*Flower tube diameter, at the base.*—About 2.5 mm.

*Flower buds.*—Length: About 1.2 cm. Diameter: About 3 mm. Shape: Oblong. Color: Close to 145C; towards the apex, close to N78A to N78D.

*Petals.*—Arrangement: Single whorl of five petals, fused; three larger lower petals and two smaller upper petals. Three lower petals: Length, above throat: About 1.3 cm. Width: About 6 mm. Two upper petals: Length, above throat: About 8 mm. Width: About 4 mm. Upper and lower petals: Shape: Oblong. Apex: Cuspidate. Margin: Entire. Texture, upper and lower surfaces: Smooth, glabrous. Color, upper and lower petals: When opening, upper surface: Close to N80A; towards the margins, close to N81A. When opening, lower surface: Close to N80B to N80D; towards the margins, close to N81A to N81D. Fully opened, upper surface: Close to N80A; towards the margins, close to N81A. Fully opened, lower surface: Close to N85A to N85D; towards the margins, close to N80A to N80D. Throat: Close to 85B to 85D; venation, close to N79C. Tube: Close to 85D. Eye: Close to 155C; spots, close to N79C; stripes, close to 144A.

*Sepals.*—Arrangement: Single whorl of five sepals, fused at the base; star-shaped calyx. Length: About 6.3 mm. Width: About 1.2 mm. Shape: Acicular. Apex: Acute. Margin: Entire. Texture, upper and lower surfaces: Smooth, glabrous. Color, upper surface: Close to 147A tinted with close to N79B. Color, lower surface: Close to 147A.

*Peduncles.*—Length: About 21 cm. Diameter: About 1.3 mm. Strength: Strong, flexible. Texture: Smooth, glabrous. Color: Close to 146A.

*Pedicels.*—Length: About 2.3 cm. Diameter: About 0.7 mm. Strength: Strong, flexible. Texture: Smooth, glabrous. Color: Close to 146A.

*Reproductive organs.*—Stamens: Quantity per flower: About five. Filament length: About 5 mm. Filament color: Close to 77A. Anther length: About 2.5 mm. Anther width: About 1.9 mm. Anther color: Close to N77A. Pollen amount: Moderate. Pollen color: Close to 8A. Pistils: Quantity per flower: One. Pistil length: About 1.1 cm. Stigma shape: Ovate. Stigma color: Close to N77A to N77B. Style length: About 6 mm. Style color: Close to 146C to 146D. Ovary color: Close to 146A.

*Seed/fruit.*—Seed and fruit production has not been observed.

Disease/pest resistance: Plants of the new *Lobelia* have not been noted to be resistant to pathogens and pests common to *Lobelia.*

Temperature tolerance: Plants of the new *Lobelia* have been observed to tolerate temperatures from about 6° C. to about 32° C.

It is claimed:

1. A new and distinct *Lobelia* plant named 'Wespurstar' as illustrated and described.

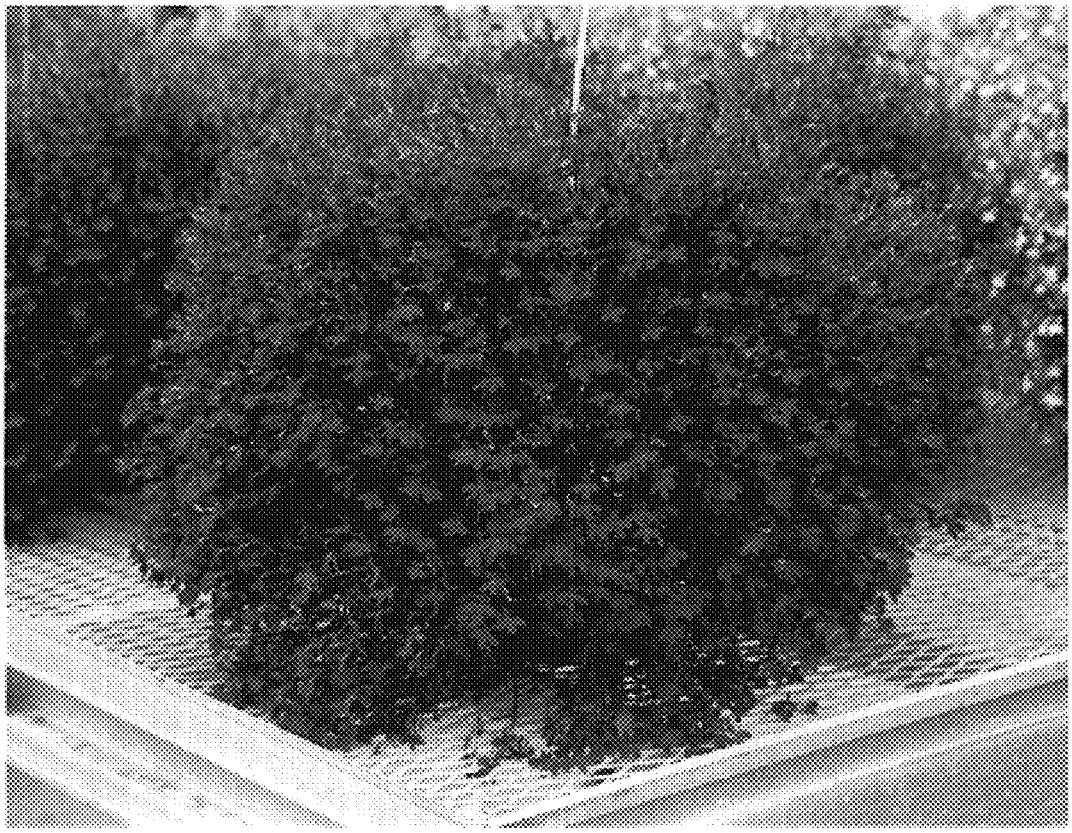
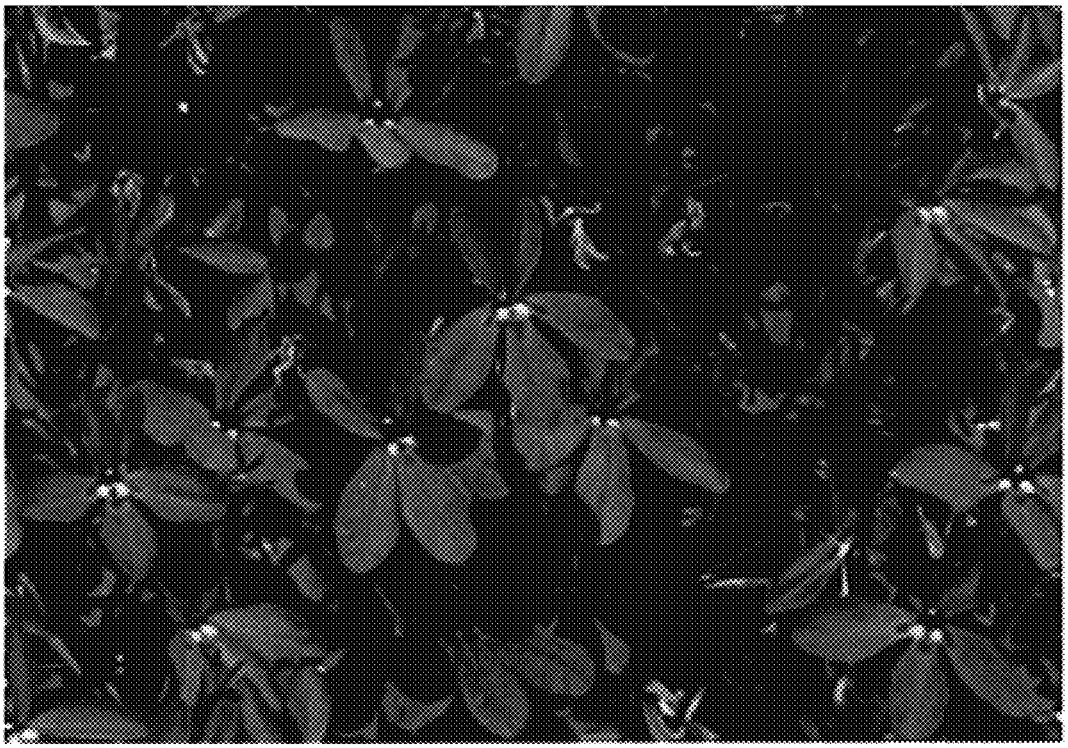

* * * * *